United States Patent [19]

Edwards et al.

[11] Patent Number: 5,720,719
[45] Date of Patent: Feb. 24, 1998

[54] ABLATIVE CATHETER WITH CONFORMABLE BODY

[75] Inventors: Stuart D. Edwards, Los Altos; Ingemar H. Lundquist, Pebble Beach, both of Calif.

[73] Assignee: Vidamed, Inc., Menlo Park, Calif.

[21] Appl. No.: 311,820

[22] Filed: Sep. 26, 1994

Related U.S. Application Data

[63] Continuation-in-part of Ser. No. 929,638, Aug. 12, 1992, abandoned, Ser. No. 12,370, Feb. 2, 1993, Pat. No. 5,370,675, Ser. No. 62,364, May 13, 1993, Pat. No. 5,435,805, Ser. No. 61,647, May 13, 1993, Pat. No. 5,421,819, Ser. No. 61,072, May 14, 1993, Pat. No. 5,385,544, Ser. No. 945,666, Sep. 16, 1992, abandoned, and Ser. No. 109,190, Aug. 19, 1993, Pat. No. 5,409,453.

[51] Int. Cl.$^6$ ................................................. A61B 17/39
[52] U.S. Cl. ............................................................. 604/22
[58] Field of Search ................................. 604/19–22, 53, 604/164, 280; 601/2; 606/39, 32, 45; 607/96, 113, 115, 116, 138, 156, 101, 102

[56] References Cited

U.S. PATENT DOCUMENTS

| | | |
|---|---|---|
| 32,066 | 1/1861 | Leveen. |
| 1,879,249 | 9/1932 | Hansaker ........................ 604/280 |
| 1,950,788 | 3/1934 | Ewerhardt et al.. |
| 1,968,997 | 8/1934 | Drucker. |
| 2,008,526 | 7/1935 | Wappler et al.. |
| 2,022,065 | 11/1935 | Wappler. |
| 2,047,535 | 7/1936 | Wappler. |
| 2,118,631 | 5/1938 | Wappler. |
| 2,710,000 | 6/1955 | Cromer et al.. |
| 3,230,957 | 1/1966 | Seifert. |
| 3,339,542 | 9/1967 | Howell. |
| 3,556,079 | 1/1971 | Omizo et al. ........................ 128/2 |
| 3,595,239 | 7/1971 | Petersen. |
| 3,598,108 | 8/1971 | Jamshidi et al.. |
| 3,682,162 | 8/1972 | Colyer. |
| 3,828,780 | 8/1974 | Morrison, Jr.. |
| 3,835,842 | 9/1974 | Iglesias. |
| 3,840,016 | 10/1974 | Lindemann. |
| 3,850,175 | 11/1974 | Iglesias. |
| 3,858,577 | 1/1975 | Bass et al.. |
| 3,884,237 | 5/1975 | O'Malley et al.. |
| 3,924,628 | 12/1975 | Droegemueller et al.. |
| 3,939,840 | 2/1976 | Storz. |
| 3,941,121 | 3/1976 | Olinger et al.. |

(List continued on next page.)

FOREIGN PATENT DOCUMENTS

| | | |
|---|---|---|
| 1085892 | 8/1992 | Australia. |
| 0219216 A1 | 4/1987 | European Pat. Off.. |
| 0370890 | 5/1990 | European Pat. Off.. |
| 0453071 | 10/1991 | European Pat. Off.. |
| 0495443 | 7/1992 | European Pat. Off.. |
| 521264A2 | 1/1993 | European Pat. Off.. |
| 2848484 | 5/1979 | Germany. |
| 2941060A1 | 4/1980 | Germany. |
| 3218314 | 6/1983 | Germany. |
| 3247793A1 | 7/1983 | Germany. |

(List continued on next page.)

OTHER PUBLICATIONS

Standard Urology Product Catalog, Circon ACMI: Stanford (1992).

Chang, Raymond J. et al, American Heart Journal, 125: 1276–1283 (May, 1993).

Cosman, Eric R. et al., Sterostatic and Functional Neurosurgery, pp. 2490–2499 (Date Unknown).

Diasonics, Brochure DIA 2000 171 CRF May 1988.

(List continued on next page.)

*Primary Examiner*—Manuel Mendez
*Attorney, Agent, or Firm*—Flehr, Hohbach, Test, Albritton & Herbert

[57] ABSTRACT

A medical probe device for reducing tissue mass in a selected portion of the body comprises a catheter having a control end and a probe end. The probe end includes a malleable tube and a flexible tube that allow the probe end to conform to the curvature of the cavity inside a patient's body.

14 Claims, 4 Drawing Sheets

U.S. PATENT DOCUMENTS

| | | |
|---|---|---|
| 3,942,530 | 3/1976 | Northeved . |
| 3,948,270 | 4/1976 | Hasson . |
| 3,991,770 | 11/1976 | Leveen . |
| 4,011,872 | 3/1977 | Komiya . |
| 4,119,102 | 10/1978 | Leveen . |
| 4,121,592 | 10/1978 | Whalley . |
| 4,136,566 | 1/1979 | Christensen . |
| 4,137,920 | 2/1979 | Bonnet . |
| 4,154,246 | 5/1979 | Leveen . |
| 4,204,549 | 5/1980 | Paglione . |
| 4,224,929 | 9/1980 | Furihata . |
| 4,228,809 | 10/1980 | Paglione ............................ 128/804 |
| 4,237,898 | 12/1980 | Whalley . |
| 4,267,828 | 5/1981 | Matsuo . |
| 4,295,467 | 10/1981 | Mann et al. . |
| 4,307,720 | 12/1981 | Weber, Jr. . |
| 4,311,145 | 1/1982 | Esty et al. . |
| 4,311,154 | 1/1982 | Sterzer et al. . |
| 4,312,364 | 1/1982 | Convert et al. . |
| 4,336,809 | 6/1982 | Clark . |
| 4,375,220 | 3/1983 | Matvias . |
| 4,397,314 | 8/1983 | Vaguine . |
| 4,402,311 | 9/1983 | Hattori . |
| 4,405,314 | 9/1983 | Cope . |
| 4,411,266 | 10/1983 | Cosman . |
| 4,448,198 | 5/1984 | Turner . |
| 4,452,236 | 6/1984 | Utsugi . |
| 4,470,407 | 9/1984 | Hussein ............................ 606/2 |
| 4,494,539 | 1/1985 | Zenitani et al. . |
| 4,552,554 | 11/1985 | Could et al. . |
| 4,562,838 | 1/1986 | Walker . |
| 4,565,200 | 1/1986 | Cosman . |
| 4,568,329 | 2/1986 | Mahurkar . |
| 4,580,551 | 4/1986 | Siegmund et al. . |
| 4,594,074 | 6/1986 | Anderson et al. . |
| 4,601,296 | 7/1986 | Yerushalmi . |
| 4,612,940 | 9/1986 | Kasevich et al. . |
| 4,658,836 | 4/1987 | Turner . |
| 4,660,560 | 4/1987 | Klein . |
| 4,669,475 | 6/1987 | Turner . |
| 4,672,962 | 6/1987 | Hershenson . |
| 4,676,258 | 6/1987 | Inokuchi et al. . |
| 4,681,122 | 7/1987 | Winters et al. . |
| 4,682,596 | 7/1987 | Bales et al. . |
| 4,697,595 | 10/1987 | Breyer et al. . |
| 4,700,716 | 10/1987 | Kasevich et al. . |
| 4,706,681 | 11/1987 | Breyer et al. . |
| 4,709,698 | 12/1987 | Johnston et al. . |
| 4,719,914 | 1/1988 | Johnson . |
| 4,753,223 | 6/1988 | Bremen ............................ 604/95 |
| 4,765,331 | 8/1988 | Petruzzi et al. . |
| 4,769,005 | 9/1988 | Ginsburg et al. . |
| 4,774,949 | 10/1988 | Fogarty . |
| 4,776,086 | 10/1988 | Kasevich et al. . |
| 4,781,186 | 11/1988 | Simpson et al. . |
| 4,784,638 | 11/1988 | Ghajar et al. . |
| 4,785,829 | 11/1988 | Convert et al. . |
| 4,798,215 | 1/1989 | Turner . |
| 4,800,899 | 1/1989 | Elliott . |
| 4,805,616 | 2/1989 | Pao . |
| 4,813,429 | 3/1989 | Eshel et al. . |
| 4,817,601 | 4/1989 | Roth et al. . |
| 4,818,954 | 4/1989 | Flachenecker et al. . |
| 4,822,333 | 4/1989 | Lavarenne . |
| 4,823,791 | 4/1989 | D'Amelio et al. . |
| 4,823,812 | 4/1989 | Eshel et al. . |
| 4,860,744 | 8/1989 | Johnson et al. . |
| 4,865,017 | 9/1989 | Chou et al. . |
| 4,872,458 | 10/1989 | Kanehira et al. . |
| 4,887,615 | 12/1989 | Taylor . |
| 4,893,623 | 1/1990 | Rosenbluth . |
| 4,896,671 | 1/1990 | Cunningham et al. . |
| 4,898,577 | 2/1990 | Badger . |
| 4,905,667 | 3/1990 | Foerster et al. . |
| 4,906,230 | 3/1990 | Maloney et al. . |
| 4,907,589 | 3/1990 | Cosman . |
| 4,911,148 | 3/1990 | Sosnowski et al. . |
| 4,911,173 | 3/1990 | Terwilliger . |
| 4,919,129 | 4/1990 | Weber, Jr. et al. . |
| 4,920,978 | 5/1990 | Colvin . |
| 4,932,958 | 6/1990 | Reddy et al. . |
| 4,936,281 | 6/1990 | Stasz . |
| 4,940,064 | 7/1990 | Desai . |
| 4,943,290 | 7/1990 | Rexroth ............................ 606/49 |
| 4,946,449 | 8/1990 | Davis, Jr. . |
| 4,949,706 | 8/1990 | Thon . |
| 4,950,267 | 8/1990 | Ishihara et al. . |
| 4,955,877 | 9/1990 | Lennox et al. . |
| 4,961,435 | 10/1990 | Kitagawa et al. . |
| 4,966,597 | 10/1990 | Cosman . |
| 4,967,765 | 11/1990 | Turner et al. . |
| 4,982,724 | 1/1991 | Saito et al. . |
| 4,994,062 | 2/1991 | Nishigaki et al. . |
| 4,998,923 | 3/1991 | Samson et al. ............................ 604/95 |
| 4,998,932 | 3/1991 | Rosen et al. . |
| 4,998,933 | 3/1991 | Eggers et al. . |
| 5,002,558 | 3/1991 | Klein et al. . |
| 5,003,991 | 4/1991 | Takayama et al. . |
| 5,007,437 | 4/1991 | Sterzer . |
| 5,007,908 | 4/1991 | Rydell . |
| 5,010,886 | 4/1991 | Passafaro et al. . |
| 5,026,959 | 6/1991 | Ito et al. . |
| 5,029,588 | 7/1991 | Yock et al. . |
| 5,030,227 | 7/1991 | Rosenbluth et al. . |
| 5,035,695 | 7/1991 | Weber, Jr. et al. . |
| 5,035,696 | 7/1991 | Rydell . |
| 5,045,056 | 9/1991 | Behl . |
| 5,045,072 | 9/1991 | Castillo . |
| 5,055,109 | 10/1991 | Gould et al. . |
| 5,057,105 | 10/1991 | Malone et al. . |
| 5,057,106 | 10/1991 | Kasevich et al. . |
| 5,057,107 | 10/1991 | Parins . |
| 5,059,851 | 10/1991 | Corl et al. . |
| 5,060,660 | 10/1991 | Gambale et al. . |
| 5,071,418 | 12/1991 | Rosenbaum ............................ 606/45 |
| 5,080,660 | 1/1992 | Buelna . |
| 5,083,565 | 1/1992 | Parins . |
| 5,084,044 | 1/1992 | Quint . |
| 5,100,423 | 3/1992 | Fearnot . |
| 5,108,415 | 4/1992 | Pinchuk et al. . |
| 5,109,859 | 5/1992 | Jenkins . |
| 5,116,615 | 5/1992 | Gokcen et al. . |
| 5,120,316 | 6/1992 | Morales et al. . |
| 5,122,137 | 6/1992 | Lennox ............................ 606/42 |
| 5,135,525 | 8/1992 | Biscoping et al. . |
| 5,150,717 | 9/1992 | Rosen et al. . |
| 5,170,787 | 12/1992 | Lindegren . |
| 5,178,620 | 1/1993 | Eggers et al. . |
| 5,179,962 | 1/1993 | Dutcher et al. . |
| 5,190,539 | 3/1993 | Fletcher et al. . |
| 5,195,965 | 3/1993 | Shantha . |
| 5,195,968 | 3/1993 | Lundquist et al. . |
| 5,197,963 | 3/1993 | Parins ............................ 606/41 |
| 5,201,732 | 4/1993 | Parins et al. . |
| 5,207,672 | 5/1993 | Roth . |
| 5,220,927 | 6/1993 | Astrahan et al. . |
| 5,222,953 | 6/1993 | Dowlatshahi . |
| 5,228,441 | 7/1993 | Lundquist . |
| 5,234,004 | 8/1993 | Hascoet et al. ............................ 607/102 |
| 5,235,964 | 8/1993 | Abenaim . |
| 5,249,585 | 10/1993 | Turner et al. ............................ 607/99 |
| 5,254,088 | 10/1993 | Lundquist et al. . |

| Patent No. | Date | Inventor |
|---|---|---|
| 5,257,451 | 11/1993 | Edwards et al. |
| 5,273,524 | 12/1993 | Fox et al. |
| 5,273,535 | 12/1993 | Edwards et al. |
| 5,275,162 | 1/1994 | Edwards et al. |
| 5,281,213 | 1/1994 | Milder et al. |
| 5,281,217 | 1/1994 | Edwards et al. |
| 5,281,218 | 1/1994 | Imran |
| 5,287,845 | 2/1994 | Faul et al. |
| 5,290,286 | 3/1994 | Parins |
| 5,293,868 | 3/1994 | Nardella |
| 5,293,869 | 3/1994 | Edwards et al. |
| 5,299,559 | 4/1994 | Bruce et al. |
| 5,300,068 | 4/1994 | Rosar et al. |
| 5,300,069 | 4/1994 | Hunsberger et al. |
| 5,300,070 | 4/1994 | Gentelia et al. |
| 5,300,099 | 4/1994 | Rudie |
| 5,301,687 | 4/1994 | Wong et al. |
| 5,304,134 | 4/1994 | Kraus et al. |
| 5,304,214 | 4/1994 | Deford |
| 5,309,910 | 5/1994 | Edwards et al. |
| 5,312,392 | 5/1994 | Hofstetter et al. |
| 5,313,943 | 5/1994 | Houser et al. |
| 5,381,782 | 1/1995 | De La Rama et al. ................ 604/95 |

FOREIGN PATENT DOCUMENTS

| | | |
|---|---|---|
| 3844131 | 12/1988 | Germany |
| 3838840 | 5/1990 | Germany |
| 2121675 | 5/1990 | Japan |
| 9007303 | 7/1990 | WIPO |
| WO911213 | 8/1991 | WIPO |
| 9116859 | 11/1991 | WIPO |
| 9207622 | 5/1992 | WIPO |
| WO92/10142 | 6/1992 | WIPO |
| 9221278 | 12/1992 | WIPO |
| 9221285 | 12/1992 | WIPO |
| 9304727 | 4/1993 | WIPO |
| 9308755 | 5/1993 | WIPO |
| 9308756 | 5/1993 | WIPO |
| 9308757 | 10/1993 | WIPO |
| 9320767 | 10/1993 | WIPO |
| 9320768 | 10/1993 | WIPO |
| 9320886 | 10/1993 | WIPO |
| 9320893 | 10/1993 | WIPO |
| WO93/25136 | 12/1993 | WIPO |
| 9403759 | 2/1994 | WIPO |
| 9404222 | 3/1994 | WIPO |
| 9405226 | 3/1994 | WIPO |
| 9406377 | 3/1994 | WIPO |
| 9407410 | 4/1994 | WIPO |
| 9407411 | 4/1994 | WIPO |
| 9407412 | 4/1994 | WIPO |
| 9407413 | 4/1994 | WIPO |
| 9407441 | 4/1994 | WIPO |
| 9407446 | 4/1994 | WIPO |
| 9407549 | 4/1994 | WIPO |

OTHER PUBLICATIONS

Perinchery, Narayan, "Neoplasms of the Prostate Gland." pp. 378–409 (Date Unknown).

Urology 5th ed., Storz, Jan. 1992.

Transuretheral µwave Thermotherapy for Prostatism: Early Mayo Foundation Experience: Blute, Mayo Clinic Proceedings: vol. 67 May 92 pp. 417–421.

New Therapies for Benign Prostatic Hyperplasia, Editorial Bruskewitz, Mayo Clinic Proceedings vol. 67 May 92 pp. 493–495.

Industry Strategies, Urology: "A Multi Billion Dollar Market . . . " Stephen Scala Nov. 19, 1991 pp. 1–32.

U.I. Dept. of Health and Human Services, MMWR 41: 401–404 vol. 41, No. 23, (Jun. 12, 1992).

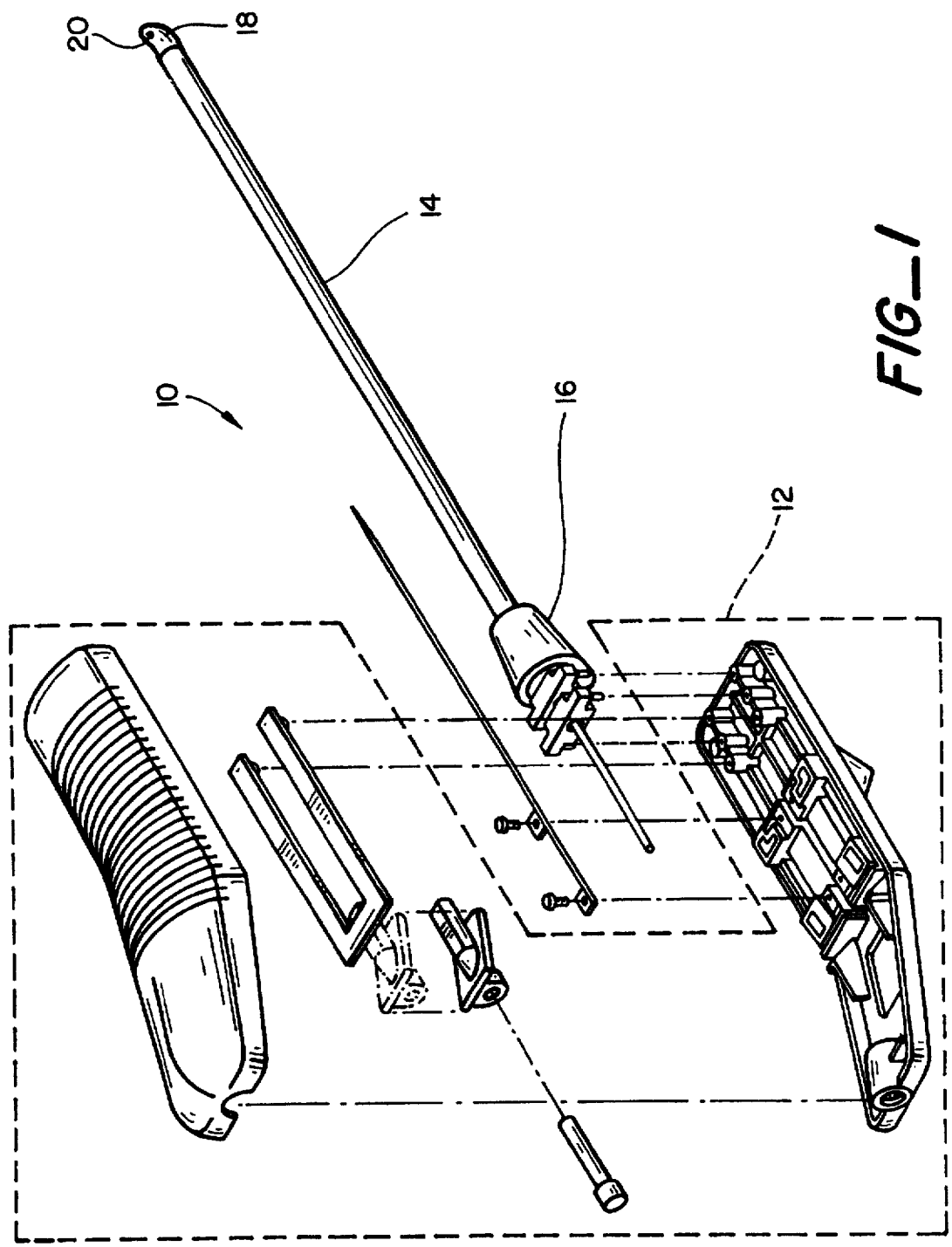

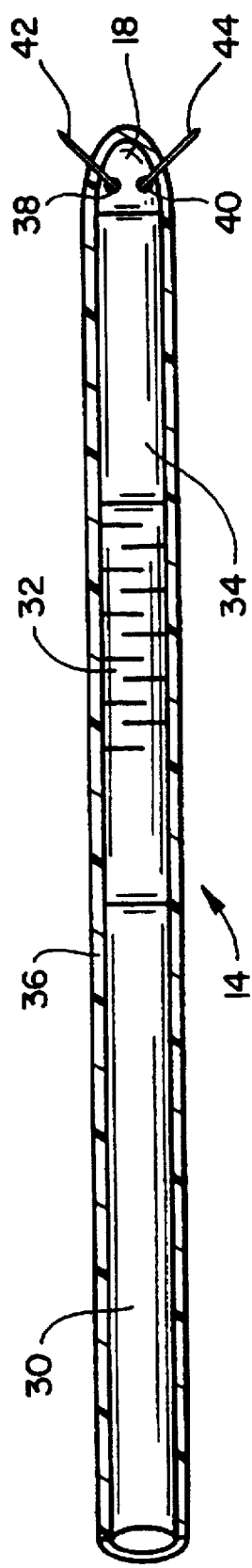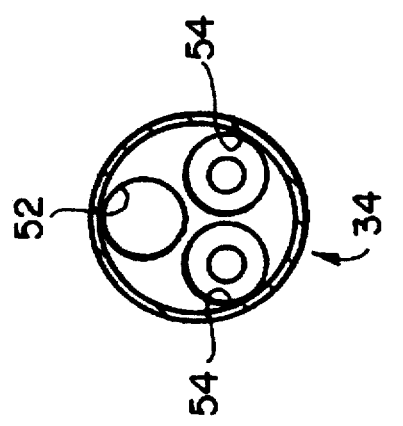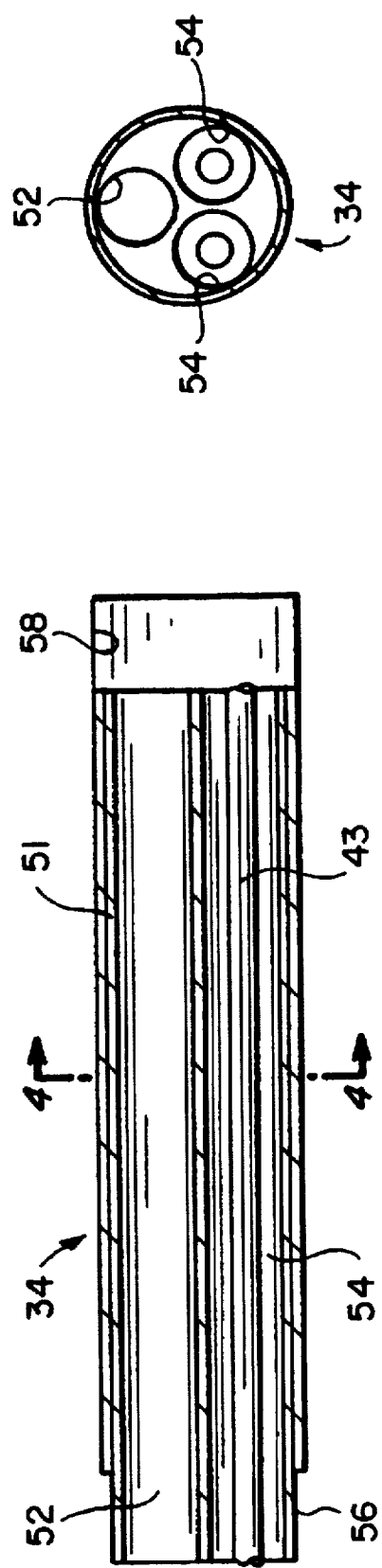
FIG_2  FIG_4  FIG_3

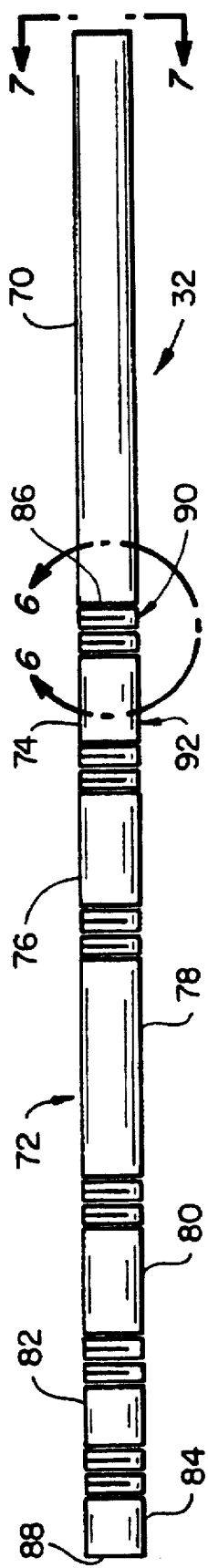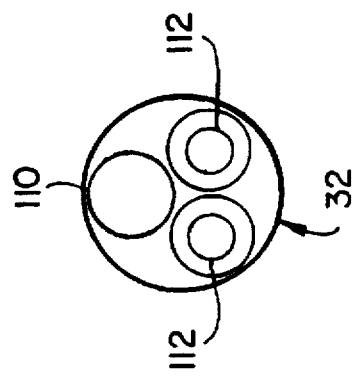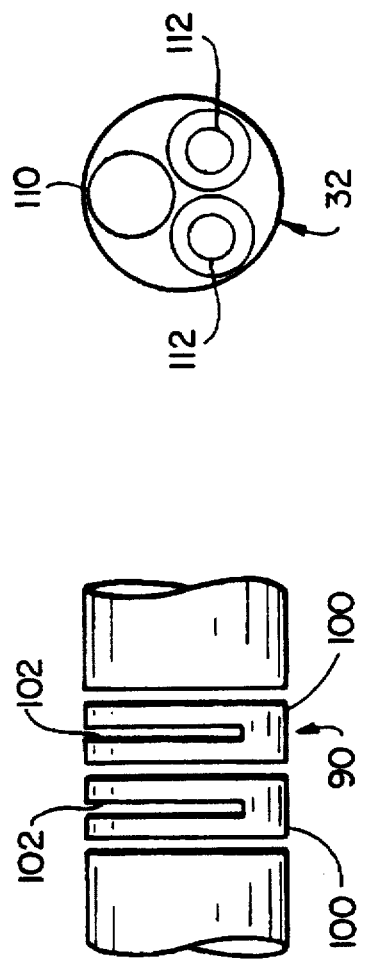

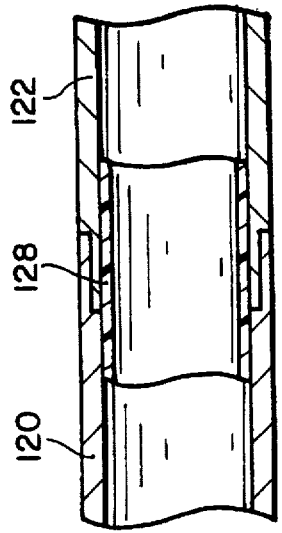
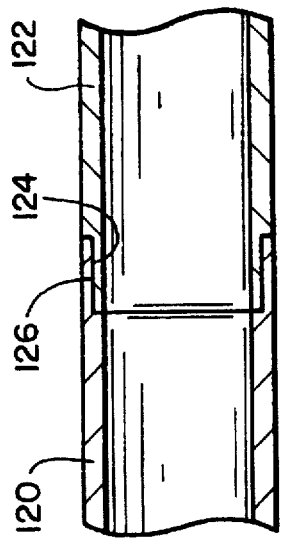
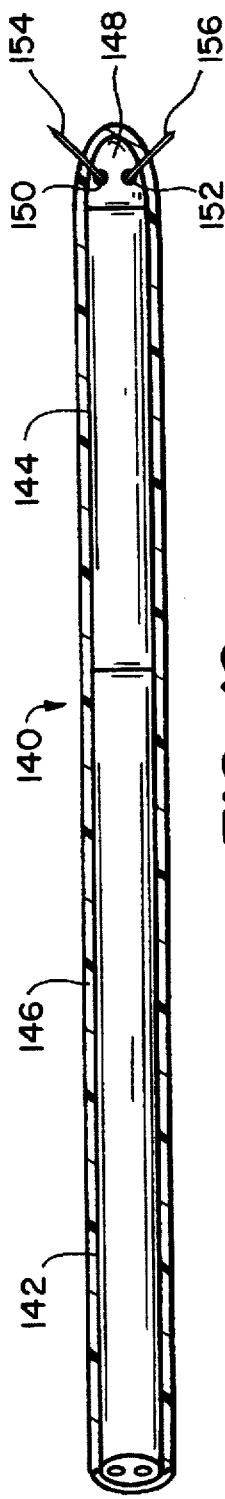
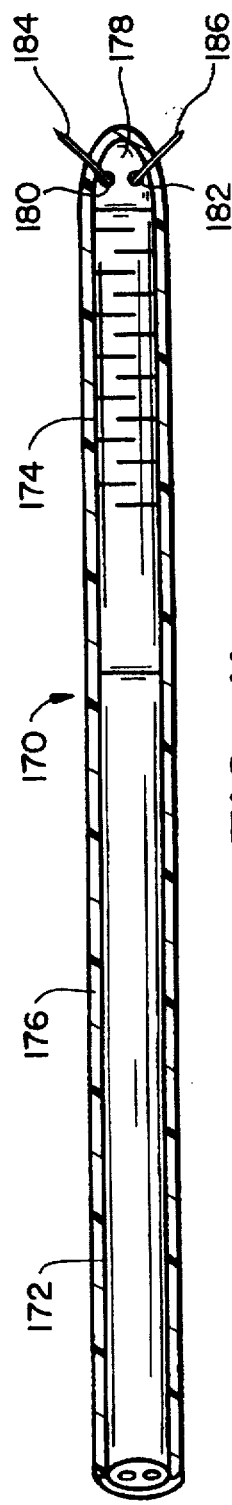

ABLATIVE CATHETER WITH CONFORMABLE BODY

This application is a continuation-in-part of applications Ser. No. 07/929,638 filed Aug. 12, 1992, abandoned in favor of Ser. No. 172,014 filed Dec. 22, 1993, now U.S. Pat. No. 5,366,490; Ser. No. 08/012,370 filed Feb. 2, 1993, now U.S. Pat. No. 5,370,675; Ser. No. 08/062,364 filed May 13, 1993, now U.S. Pat. No. 5,435,805; Ser. No. 08/061,647 filed May 13, 1993, now U.S. Pat. No. 5,421,819; Ser. No. 08/061,072 filed May 14, 1993, now U.S. Pat. No. 5,385,544; Ser. No. 07/945,666 filed Sep. 16, 1993, abandoned in favor of 126,681 filed Sep. 24, 1993, now U.S. Pat. No. 5,329,923; and Ser. No. 08/109,190 filed Aug. 19, 1993, now U.S. Pat. No. 5,409,453. The entire contents of the above applications are hereby incorporated by reference.

FIELD OF THE INVENTION

This invention is directed to a unique device for penetrating body tissues for medical purposes, such as reducing the mass of selected tissues by therapeutic ablation and fluid substance delivery. The device penetrates tissue to the precise target selected in order to deliver energy to the tissue and/or deliver substances. The penetrating portion is flexible enough to accommodate any curve within the cavity of the body. It limits this treatment to the precise preselected site, thereby minimizing trauma to normal surrounding tissue and achieving a greater medical benefit. This device includes a catheter for positioning a treatment assembly in the area or organ selected for medical treatment and one or more stylets which are mounted for extension from a stylet port in the side of the catheter through surrounding tissue to the tissue targeted for medical intervention.

BACKGROUND OF THE INVENTION

Treatment of cellular tissues usually requires direct contact of target tissue with a medical instrument, usually by surgical procedures exposing both the target and intervening tissue to substantial trauma. Often, precise placement of a treatment probe is difficult because of the location of targeted tissues in the body or the proximity of the target tissue to easily damaged, critical body organs, nerves, or other components.

Benign prostatic hypertrophy or hyperplasia (BPH), for example, is one of the most common medical problems experienced by men over 50 years old. Urinary tract obstruction due to prostatic hyperplasia has been recognized since the earliest days of medicine. Hyperplastic enlargement of the prostate gland often leads to compression of the urethra, resulting in obstruction of the urinary tract and the subsequent development of symptoms that include frequent urination, decrease in urinary flow, nocturia, pain, discomfort, and dribbling. The association of BPH with aging has been shown to exceed 50% in men over 50 years of age and increases in incidence to over 75% in men over 80 years of age. Symptoms of urinary obstruction occur most frequently between the ages of 65 and 70, when approximately 65% of men in this age group have prostatic enlargement.

Currently, there is no proven effective nonsurgical method of treatment of BPH. In addition, the surgical procedures available are not totally satisfactory. Currently, patients suffering from the obstructive symptoms of this disease are provided with few options: continue to cope with the symptoms (i.e., conservative management), submit to drug therapy at early stages, or submit to surgical intervention.

More than 430,000 patients per year undergo surgery for removal of prostatic tissue in the United States. These represent less than five percent of men exhibiting clinically significant symptoms.

Those suffering from BPH are often elderly men, many with additional health problems that increase the risk of surgical procedures. Current surgical procedures for the removal of prostatic tissue are associated with a number of hazards, including anesthesia related morbidity, hemorrhage, coagulopathies, pulmonary emboli and electrolyte imbalances. These current procedures can also lead to cardiac complications, bladder perforation, incontinence, infection, urethral or bladder neck stricture, retention of prostatic chips, retrograde ejaculation, and infertility. Due to the extensive invasive nature of the current treatment options for obstructive uropathy, the majority of patients delay definitive treatment of their condition. This circumstance can lead to serious damage to structures secondary to the obstructive lesion in the prostate (bladder hypertrophy, hydronephrosis, dilation of the kidney pelves, chronic infection, dilation of ureters, etc.), which is not without significant consequences. In addition, a significant number of patients with symptoms sufficiently severe to warrant surgical intervention are therefore poor operative risks and are poor candidates for prostatectomy. In addition, younger men suffering from BPH who do not desire to risk complications, such as infertility, are often forced to avoid surgical intervention. Thus the need, importance and value of improved surgical and non-surgical methods for treating BPH is unquestionable.

High-frequency currents are used in electrocautery procedures for cutting human tissue, especially when a bloodless incision is desired or when the operating site is not accessible with a normal scalpel but presents an access for a thin instrument through natural body openings, such as the esophagus, intestines or urethra. Examples include the removal of prostatic adenomas, bladder tumors or intestinal polyps. In such cases, the high-frequency current is fed by a surgical probe into the tissue to be cut. The resulting dissipated heat causes boiling and vaporization of the cell fluid, whereupon the cell walls rupture and the tissue is separated.

Destruction of cellular tissues in situ has been used in the treatment of many diseases and medical conditions alone or as an adjunct to surgical removal procedures. It is often less traumatic than surgical procedures and may be the only alternative where other procedures are unsafe. Ablative treatment devices have the advantage of using electromagnetic energy that is rapidly dissipated and reduced to a non-destructive level by conduction and convection forces of circulating fluids and other natural body processes.

Microwave, radiofrequency, acoustical (ultrasound) and light energy (laser) devices, as well as tissue destructive substances, have been used to destroy malignant, benign and other types of cells and tissues from a wide variety of anatomic sites and organs. Tissues treated include isolated carcinoma masses and, more specifically, organs such as the prostate, glandular and stromal nodules characteristic of benign prostate hyperplasia. These devices typically include a catheter or cannula which is used to carry a radiofrequency electrode or microwave antenna through a duct to the zone of treatment and apply energy diffusely through the duct wall into the surrounding tissue in all directions. Severe trauma is often sustained by the duct wall during this cellular destruction process, and some devices combine cooling systems with microwave antennas to reduce trauma to the ductal wall. For treating the prostate with these devices, for example, heat energy is delivered through the walls of the urethra into the surrounding prostate cells in an effort to ablate the tissue causing the constriction of the urethra. Light energy, typically from a laser, is delivered to prostate tissue target sites by "burning through" the wall of the urethra. Healthy cells of the duct wall and healthy tissue between the nodules and duct wall are also indiscriminately destroyed in the process and can cause unnecessary loss of some prostate function. Furthermore, the added cooling function of some microwave devices complicates the apparatus and requires that the device be sufficiently large to accommodate this cooling system.

Application of liquids to specific tissues for medical purposes is limited by the ability to obtain delivery without traumatizing intervening tissue and to effect a delivery limited to the specific target tissue. Localized chemotherapy, drug infusions, collagen injections, or injections of agents that are then activated by light, heat or chemicals would be greatly facilitated by a device that could conveniently and precisely place a fluid (liquid or gas) supply cannula opening at the specific target tissue.

OBJECTS AND SUMMARY OF THE INVENTION

It is an object of this invention to provide a device for penetrating tissue, through intervening tissues to the precise target tissue selected for a medical action, such as tissue ablation and/or substance delivery, limiting this activity to the precise preselected site, and thereby minimizing the trauma and achieving a greater medical benefit.

It is further an object of this invention to provide a device with a flexible intruding portion for tissue ablation of body tissues which delivers the therapeutic energy directly into targeted tissues while minimizing effects on its surrounding tissue.

It is another object of this invention to provide a device whereby its intruding portion is flexible enough to accommodate any curves or obstructions within a body cavity being penetrated.

In summary, the medical probe device for reducing tissue mass in a selected portion of the body includes a catheter having a control end and a probe end. The probe end comprises a tip having at least one stylet port. The probe end further comprises a conforming means attached between the control end and the tip for directing a flexible styler outward through the stylet port while negotiating curvatures inside a human cavity. A flexible stylet which includes a non-conductive sleeve having an electrode lumen and a second lumen therein is positioned in the probe end. The electrode lumen terminates at a distal port in the distal end of the non-conductive sleeve. A radiofrequency electrode is being positioned in the electrode lumen for longitudinal movement therein and through the distal port.

In one embodiment of this invention, the conforming means includes a malleable tube attached to a flexible tube.

In another embodiment of this invention, the conforming means includes a malleable tube.

The medical probe device is particularly useful for removing tissue mass from the prostate and can be used for treating BPH or benign or cancerous tumors of the prostate.

The device of this invention can be used in combination with a viewing scope, such as a cystoscope, endoscope, laproscope and the like, which is sized to extend therethrough.

Alternatively, the device can include a viewing scope, a fiber optic enclosed within the catheter and optic viewing means at the control end which is connected to the fiber optic.

BRIEF DESCRIPTION OF THE DRAWINGS

FIG. 1 is an exploded isometric view of an ablation device of the present invention.

FIG. 2 is a top plan view, partially cut away, of the catheter portion of the device of FIG. 1;

FIG. 3 is a cross-sectional view of the malleable tube of FIG. 2, taken along a line parallel to the longitudinal axis of the malleable tube.

FIG. 4 is cross-sectional view of the malleable tube shown in FIG. 3 taken along the line 4—4 of FIG. 3.

FIG. 5 is a side elevational view of the flexible tube of the present invention.

FIG. 6 is an enlarged side elevational/another embodiment view of a typical slotted section of a flexible portion of the flexible tube of FIG. 5 taken along the line 6—6 of FIG. 5.

FIG. 7 is an end elevational view of the flexible tube of FIG. 5 taken along line 7—7 of FIG. 5.

FIG. 8 is a cross-sectional view showing the connections between two adjacent tubes of FIG. 2.

FIG. 9 is a cross-sectional view showing another embodiment of the connections between two adjacent tubes of FIG. 2.

FIG. 10 is a top plan view, partially cut away and similar to FIG. 3, of another embodiment of the catheter portion of the device of the present invention with a malleable tube only.

FIG. 11 is a top plan view, partially cut away and similar to FIG. 3, of another embodiment of the catheter portion of the device of the present invention with a flexible tube only.

DETAILED DESCRIPTION OF THE INVENTION

The device of this invention provides a precisely controlled positioning of a treatment styler in a tissue targeted for treatment, destruction or sampling from a catheter positioned in the vicinity of the target tissue. This is described in U.S. Pat. Nos. 5,366,490 and 5,370,675 the entire contents of which are incorporated herein by reference. The device of the present invention further provides a catheter that is capable of conforming to curvatures within a body cavity.

The term "stylet" as used hereinafter is defined to include both solid and hollow probes which are adapted to be passed from a cannula port through normal tissue to targeted tissues. The stylet is shaped to facilitate easy passage through tissue. It can be a solid wire, thin rod, or other solid shape or it can be a thin hollow tube or other shape having a longitudinal lumen for introducing fluids to or removing materials from a site. The stylet can also be a thin hollow tube or other hollow shape, the hollow lumen thereof containing a reinforcing or functional rod or tube, such as a laser fiber optic. The stylet preferably has a sharpened end to reduce resistance and trauma when it is pushed through tissue to a target site.

The stylet can be designed to provide a variety of medically desired treatments of a selected tissue. As a radiofrequency electrode or microwave antenna, it can be used to ablate or destroy targeted tissues. As a hollow tube, it can be used to deliver a treatment fluid such as a liquid to targeted tissues. The liquid can be a simple solution or a suspension of solids, for example, colloidal particles, in a liquid. Since the stylet is very thin, it can be directed from the cannula through intervening normal tissue with a minimum of trauma to the normal tissue.

The device of this invention provides a more precise, controlled medical treatment which is suitable for destroying cells of medically targeted tissues throughout the body, both within and external to body organs. The device is particularly useful for treating benign prostate hyperplasia (BPH), and the device and its use are hereinafter described with respect to BPH, for purposes of simplifying the description thereof. It will be readily apparent to a person skilled in the art that the device can be used to destroy body tissues in any body cavities or tissue locations that are accessible by percutaneous or endoscopic catheters, and is not limited to the prostate. Application of the device in all of these organs and tissues is intended to be included within the scope of this invention.

BPH is a condition that arises from the replication and growth of cells in the prostate and the decrease of cell death rate, forming glandular and stromal nodules which expand the prostate and constrict the opening of the prostatic urethra. Glandular nodules are primarily concentrated within the transition zone, and stromal nodules within the periurethral region. Traditional treatments of this condition have included surgical removal of the entire prostate gland, digital removal of the adenoma, as well as transurethral resection of the urethral canal and prostate to remove tissue and widen the passageway. One significant and serious complication associated with these procedures is iatrogenic sterility. More recently, laser treatment has been employed to remove tissue, limiting bleeding and loss of body fluids. Balloons have also been expanded within the urethra to enlarge its diameter, with and without heat, but have been found to have significant limitations.

Microwave therapy has been utilized with some success by positioning a microwave antenna within the prostatic urethra and generating heat in the tissue surrounding the urethra with an electromagnetic field. Coolants are sometimes applied within the catheter shaft to reduce the temperature of the urethral wall. This necessitates complicated mechanisms to provide both cooling of the immediately adjacent tissues while generating heat in the more distant prostatic tissue. This technique is similar to microwave hyperthermia. Similarly, radiofrequency tissue ablation with electrodes positioned within the urethra exposes the urethral wall to destructive temperatures. To avoid this, low temperature settings required to protect the urethra must be so low that the treatment time required to produce any useful effect is unduly extended, e.g. up to three hours of energy application.

The device of this invention accesses the prostate through the urethra and positions RF electrode stylets directly into the tissues to be destroyed. The portion of the stylet conductor extending from the urethra to targeted tissues is enclosed within a longitudinally adjustable sleeve shield which prevents exposure of the tissue adjacent to the sleeve to the RF current. The sleeve movement controls the amount of electrode exposed, which is used to control the amount of energy per unit surface area that is delivered to the target tissue. Thus, the ablative destruction is confined to the tissues targeted for destruction, namely those causing the constriction. Other aspects of the invention will become apparent from the drawings and accompanying descriptions of the device of this invention. It will be readily apparent to a person skilled in the art that this procedure can be used in many areas of the body for percutaneous approaches and approaches through body orifices.

Further details about the preferred embodiments of the invention will become evident in conjunction with the description of the drawings.

FIG. 1 shows a medical device 10 according to the present invention. The medical device 10 includes a catheter 14 connected to a control unit 12 by means of a connector 16. A tip 18 is connected to the distal end of the catheter 14. Tip 18 includes at least one port 20 which allows the stylet to protrude and contact the target issue.

FIG. 2 is a top plan view, partially cut away view of catheter 14. It shows the specific parts of a typical example of catheter 14. Catheter 14 includes steel tube 30, flexible tube 32 which is connected to the distal end of steel tube 30, malleable tube 34 which is connected to the distal end of flexible tube 32, and a polymeric outer layer 36. Catheter 14 further includes tip 18, stylet ports 38 and 40, and electrodes 42 and 44.

As disclosed in the above-mentioned co-pending applications, catheter 14 includes tubings (not shown) which allow the stylets to be extended inside the patient's body. The stylets include a flexible sleeve 43 which enclose radiofrequency ("RF") electrodes. RF electrodes 42 and 44 are used to deliver the ablative energy to the target tissue. The electrodes are extended outward through ports 38 and 40 to contact the selected tissues. Although two ports are shown in FIG. 2, catheter 14 could have one port or more than two ports. The number of electrodes is preferably the same as the number of ports.

As previously mentioned, existing catheters are not easily bendable to provide easier insertion into a body cavity. This forces the body to continuously adjust to allow the catheter to be extended toward a target tissue. The present invention provides a catheter that is easily bendable for easier insertion into the body cavity.

The above capability facilitates insertion of the catheter by the physician. The flexibility present in catheter 14 of the present invention prevents unnecessary trauma to the patient's body. The overall flexibility of the catheter of the present invention is provided by two separate sections. Flexible tube 32 provides the capability of flexure after it is inserted inside the cavity. Malleable tube 34 provides the capability of changing the orientation of catheter 14 before it is inserted inside the cavity. The change in the orientation is permanent until the user changes the orientation of catheter 14.

Depending on the requirement of catheter 14, malleable tube 34 could have different paths or lumens for routing stylers or probes through the catheter. FIG. 3 is a cross-sectional view of an example of malleable tube 34 in FIG. 2, showing different lumens provided therein. FIG. 4 is a cross-sectional view of the malleable tube shown in FIG. 3 taken along the line 4—4 of FIG. 3. Malleable tube 34 includes a cylindrical housing 510 optical path or lumen 52, and stylet paths or lumens 54. Malleable tube 34 also includes mating surfaces 56 and 58. Although, two stylet paths 54 are shown in FIG. 4, the present invention could include only one stylet path or more than two stylet paths. The choice of the number of stylet paths depends on the specific requirements of the medical device 10.

For malleable tube 34 to be easily bendable, it must be made of materials that are easily deformed such as copper or equivalent malleable metal or plastic.

As shown in FIG. 3, malleable tube 34 includes mating surfaces 56 and 58. They are provided to facilitate the connection between the two adjacent tubes, for example, malleable tube 34 and flexible tube 32. The detail description of different methods of connecting the two adjacent tubes will be explained hereinafter.

As described above, slotted flexible tube 32 provides the capability of flexing catheter 14 while it is inside a body cavity. Suitable slotted tubes and methods for their manufacture are described in U.S. Pat. Nos. 4,642,098, 5,195,968, 5,228,441, 5,243,167, 5,315,996 and 5,322,064, the entire contents of which are hereby incorporated by reference.

FIG. 5 is another embodiment of flexible tube 32. Flexible tube 32 includes a solid tube section 70 and flexible tube section 72 having flexible portions spaced apart longitudinally between its proximal and distal ends 86 and 88. Each flexible portion 74, 76, 78, 80, 82 and 84 includes a slotted section 90 and a solid section 92. The length of slotted section 90 and solid section 92 of each flexible portion depends on the requirement of the flexible tube 32. Furthermore, the length of slotted section 90 and solid section 92 can differ from one flexible portion to the next.

FIG. 6 is an enlarged view of a typical slotted section 90. Each slotted section 90 includes at least one and preferably more than one short cylinder 100. Each short cylinder 100 includes a radial slot 102 positioned between its two ends. The width of each radial slot 102 depends on the requirement of the catheter. Radial slot 102 subtends less than one circumference of short cylinder 102 wall, or in other words less than 360°.

In order to obtain flexibility in all directions, the open end of radial slot 102 of different slotted section 92 must be aligned at different angles. For example, in FIG. 6, the open ends of radial slots 102 are aligned such that an axis through the slots is perpendicular to the longitudinal axis of flexible tube 32. The open ends of slots of the slotted section in the next flexible portion could be provided at a 60° angle with respect to the longitudinal axis of flexible tube 32.

The desired degree of flexibility in a flexible portion can be varied by providing fewer or more slots 102 in that flexible portion. Thus, there can be provided as few as a single slot to a total of 10 or more slots. For example, the slotted section of flexible portion 84 could have 15 slots, the slotted section of flexible portion 82 could have 15 slots, the slotted section of flexible portion 80 could have 20 slots, the slotted section of flexible portion 78 could have 23 slots, and the slotted section flexible portion 76 could have 20 slots and the slotted section of flexible portion 74 could have 15 slots. The width of each slot of a particular flexible tube depends on the requirement of the catheter using the flexible tube 32. For example, each slot in flexible portion 84 is 0.040 inches wide.

In the present invention, flexible tube 32 is preferably made of stainless steel, or other metal or plastic materials having the same characteristics.

Referring to FIG. 2, thin polymeric coating or film layer 36 encapsulates the outer surface of catheter 14. Coating 36 is very flexible and permits desired flexing of the flexible tube 32 and malleable tube 34. In the case of flexible tube 32, coating 36 prevents undue bending or stress in the material of the side wall in any one slot and thereby prevents the placement of a permanent strain in any portion of the tube. In other words, the coating 36 prevents bending or flexing of flexible tube 32 beyond the point from which it will not return to its original configuration. Coating 36 also serves to prevent blood or any other liquid in the cavity in which the catheter is introduced from entering into slots 102 and caused possible clotting.

The coating or film layer 36 can be formed by applying a polymeric film-forming solution to the surface of the catheter. Alternatively, the catheter can be enclosed in a thin, shrinkable tubing which is shrunk As seen in FIG. 6, short cylinders 100 of each flexible portion are not attached to the respective solid portions 92. Coating 36 also provides the means to align all the pieces of flexible tubes and keep them intact.

Similar to malleable tube 34, flexible tube 32 may include an optical path or lumen and/or stylet paths. The availability of any or all of the above paths depends on the design of the catheter 14. FIG. 7 is an end view of flexible tube 32 which shows an example of the paths provided inside flexible tube 32. In the example of FIG. 7, flexible tube 32 includes an optical lumen or path 110 and stylet paths or lumens 112.

FIG. 8 is a cross-sectional view taken along the longitudinal axis of catheter 14 (FIG. 2) showing the junctions between adjacent tube sections of stainless steel or equivalent metal or plastic. Tubes 120 and 122 can be any one of different tube sections used to form catheter 14 (FIG. 2) and, for example, can include surfaces such as mating surfaces 58 and 122 shown in FIG. 3. Both mating surfaces 124 and 126 are complementary. Each one of the tubes 120 or 122 includes a mating surface 124 along 180° of the tube wall and a mating surface 126 along the opposite 180° of the other tube wall. This allows the particular tube to be able to connect to the adjacent tubes on either of its two sides.

To connect tubes 120 and 122, they are joined such that surface 124 mates with surface 126. The connection between two adjacent tubes is sealed using any one of the readily available sealing methods. For example, epoxy resin adhesive could be used to seal the connection between tubes 120 and 122. In this method, epoxy resin is applied to two mating surfaces. Thereafter, it is cured to create a bending between the two mating surfaces. An alternative method is to solder the connection between the two mating surfaces 124 and 126.

FIG. 9 shows an alternative tube joinder method wherein an inner tube section 128 made of urethane plastic or the like presses outward against the inner surface of the adjacent tubes 120 and 122, clamping the tubes together.

The flexible and malleable tube sections 34 and 36 shown in FIG. 2 can be used together or alone. FIG. 10 is a top plan view, partially cut away, of a catheter 140 which only incorporates a malleable tube. Catheter 140 includes steel tube 142, malleable tube 144 which is connected to the distal end of steel tube 142, and coating 146. Catheter 140 further includes tip 148, ports 150 and 152, and electrodes 154 and 156. Catheter 140 enables the user to deform its orientation before inserting it inside a body cavity. However, once inside the cavity, it does not have flexibility to accommodate incidental curvatures.

FIG. 11 is a top plan view, partially cut away, of a catheter 170 which includes flexible tube 174 as part of its structure. Catheter 170 includes steel tube 172, flexible tube 174 which is connected to the distal end of steel tube 172, and coating 176. Catheter 170 further includes tip 178, ports 180 and 182, and electrodes 184 and 186. Catheter 170 is able to accommodate incidental curvatures once it is inside a body cavity.

Thus, a medical device having a catheter which includes flexible and malleable tubes has been presented with respect to specific embodiments. The flexible and malleable tubes provide the capability of conforming the catheter to the inside curves of a body cavity. Other variations of the present invention are obvious to one knowledgeable in the art. For example, the order of connecting the flexible tube and the malleable tube could be reversed based on the requirement of the medical device. Therefore, the present invention is not to be limited except by the appended claims.

The invention claimed is:

1. A medical probe device for treatment by radio frequency ablation of tissue in a prostate of a human male having a urethra with curves therein, the tissue of the prostate surrounding a portion of the urethra, comprising an elongate tubular member having proximal and distal extremities, the elongate tubular member being sized to be able to enter the urethra and having a length so that when the distal extremity is disposed in the vicinity of the prostate the proximal extremity is outside of the urethra, the elongate tubular member having a passageway extending between its proximal and distal extremities, a radio frequency needle electrode of an electrically conductive material slidably disposed in the passageway, a sleeve of insulating material coaxially disposed on the needle electrode, means carried by the distal extremity of the elongate tubular member and in communication with the passageway for directing the needle electrode and the insulating sleeve sidewise of the elongate tubular member and into the tissue of the prostate and a handle secured to the proximal extremity of the elongate tubular member, at least a portion of the elongate tubular member being sufficiently bendable to permit the elongate tubular member to assume a curved shape which passes more easily through the curves of the urethra.

2. A device of claim 1 wherein the portion of the elongate tubular member is fabricated from copper.

3. A device of claim 1 wherein the portion of the elongate tubular member includes one or more flexible slotted tube portions.

4. A device of claim 1 wherein the elongate tubular member includes one or more stylet lumen, a thermocouple lumen, an optical lumen, or a combination thereof.

5. A device of claim 1 wherein the means for directing the needle electrode and the insulating sleeve sidewise of the elongate tubular member includes a tip carried by the distal extremity of the elongate tubular member and provided with at least one stylet port, the needle electrode being retained within the passageway of the elongate tubular member and being directed outward from the elongate tubular member through the stylet port into the tissue of the prostate.

6. A device of claim 1 together with an additional radio frequency needle electrode of an electrically conductive material and a sleeve of insulating material coaxially disposed on the additional needle electrode, means carried by the elongate tubular member for providing a first lumen in the elongate tubular member for slidably receiving the first named needle electrode and for providing a second lumen in the elongate tubular member for slidably receiving the additional needle electrode.

7. A device of claim 6 further comprising means carried by the elongate tubular member for providing a third lumen in the elongate tubular member for receiving an optical element of an endoscope.

8. A device of claim 1 wherein the insulating sleeve is slidably disposed on the needle electrode.

9. A medical probe device for treatment by radio frequency ablation of tissue in a prostate of a human male having a urethra with curves therein, the tissue of the prostate surrounding a portion of the urethra, comprising a catheter shaft having proximal and distal extremities, the catheter shaft having a tip which includes first and second stylet ports, the catheter shaft being sized to be able to enter the urethra and having a length so that when the distal extremity is disposed in the vicinity of the prostate the proximal extremity is outside of the urethra, the catheter shaft having at least one lumen extending between its proximal and distal extremities in communication with the first and second stylet ports, first and second radio frequency needle electrodes of an electrically conductive material slidably disposed in the at least one lumen, a sleeve of insulating material coaxially disposed on each of the needle electrodes whereby the tip serves to direct the first and second needle electrodes and insulating sleeves sidewise of the catheter shaft out of the stylet ports and into the tissue of the prostate and a handle secured to the proximal extremity of the catheter shaft, at least a portion of the catheter shaft being sufficiently flexible to follow a curved path when passed through the curves of the urethra.

10. A device of claim 9 wherein the flexible portion of the catheter shaft is fabricated from slotted stainless steel tubing.

11. A device of claim 9 wherein the flexible portion of the catheter shaft is sufficiently malleable to permit said portion to be bent prior to insertion into the urethra to a curved shape which passes more easily through a curve of the urethra.

12. A device of claim 9 wherein the catheter shaft is further provided with a thermocouple lumen, an optical lumen, or a combination thereof.

13. A medical probe device for treatment by radio frequency ablation of tissue in a prostate of a human male having a urethra with curves therein, the tissue of the prostate surrounding a portion of the urethra, comprising an elongate tubular member having proximal and distal extremities, the elongate tubular member having a length so that when the distal extremity is disposed in the vicinity of the prostate the proximal extremity is outside of the urethra, at least a portion of the elongate tubular member being made from bendable plastic, a handle secured to the proximal extremity of the elongate tubular member, the elongate tubular member having at least first and second lumens extending between its proximal and distal extremities, the elongate tubular member having a tip with first and second side ports in communication with the first and second lumens, a radio frequency needle electrode of an electrically conductive material slidably disposed in each of the lumens in the elongate tubular member whereby the tip directs the needle electrodes sidewise of the elongate tubular member out of the stylet ports and into the tissue of the prostate for creating lesions therein.

14. A device of claim 14 together with a sleeve of insulating material slidably disposed on each of the needle electrodes.

* * * * *